US00PP23834P2

(12) United States Plant Patent
Momparler Albors

(10) Patent No.: US PP23,834 P2
(45) Date of Patent: Aug. 13, 2013

(54) *LAVANDULA* PLANT NAMED 'MOMPARLER'

(50) Latin Name: *Lavandula angustifolia*
Varietal Denomination: Momparler

(76) Inventor: Juan Ismael Momparler Albors, Castelló de Rugat (ES)

( * ) Notice: Subject to any disclaimer, the term of this patent is extended or adjusted under 35 U.S.C. 154(b) by 104 days.

(21) Appl. No.: 13/200,604

(22) Filed: Sep. 24, 2011

(51) Int. Cl.
*A01H 5/00* (2006.01)

(52) U.S. Cl.
USPC ..... Plt./445

(58) Field of Classification Search
USPC ..... Plt./445, 226
See application file for complete search history.

(56) References Cited

PUBLICATIONS

Pluto Upov Plant Variety Database 2012/06, retrieved from the Internet at <http://www.upov.int/pluto/en/index.jsp> retrieved on Feb. 14, 2012, citation for Lavandula 'Momparler', 2 pp.*

* cited by examiner

*Primary Examiner* — June Hwu
(74) *Attorney, Agent, or Firm* — C. A. Whealy

(57) ABSTRACT

A new and distinct cultivar of *Lavandula* plant named 'Momparler', characterized by its compact and upright plant habit; freely basal branching growth habit; dense and bushy plant form; greyed green and pale yellow variegated leaves; freely flowering habit; violet blue-colored flowers; and good garden performance.

3 Drawing Sheets

Botanical designation: *Lavandula angustifolia.*
Cultivar denomination: 'MOMPARLER'.

BACKGROUND OF THE INVENTION

The present invention relates to a new and distinct cultivar of *Lavandula* plant, botanically known as *Lavandula angustifolia* and hereinafter referred to by the name 'Momparler'.

The new *Lavandula* plant is a naturally-occurring branch mutation of an unnamed selection of *Lavandula angustifolia*, not patented. The new *Lavandula* plant was discovered and selected by the Inventor in March, 2006 on a single plant of the parent selection within a population of plants of the parent selection in a controlled outdoor nursery environment in Aielo de Rugat, Valencia, Spain.

Asexual reproduction of the new *Lavandula* plant by terminal cuttings in a controlled environment in Aielo de Rugat, Valencia, Spain since March, 2006 has shown that the unique features of this new *Lavandula* plant are stable and reproduced true to type in successive generations.

SUMMARY OF THE INVENTION

Plants of the new *Lavandula* have not been observed under all possible environmental conditions and cultural practices. The phenotype may vary somewhat with variations in environmental conditions such as temperature and light intensity, without, however, any variance in genotype.

The following traits have been repeatedly observed and are determined to be the unique characteristics of 'Momparler'. These characteristics in combination distinguish 'Momparler' as a new and distinct *Lavandula* plant:

1. Compact and upright plant habit.
2. Freely basal branching growth habit; dense and bushy plant form.
3. Greyed green and pale yellow variegated leaves.
4. Freely flowering habit.

5. Violet blue-colored flowers.
6. Good garden performance.

Plants of the new *Lavandula* differ from plants of the parent selection primarily in leaf color as plants of the parent selection do not have variegated leaves.

Plants of the new *Lavandula* can be compared to plants of *Lavandula angustifolia* 'Blue Royalty', disclosed in U.S. Plant Pat. No. 20,657. Plants of the new *Lavandula* differ from plants of 'Blue Royalty' primarily in leaf and flower color as plants of 'Blue Royalty' have green-colored leaves and dark purple-colored flowers.

BRIEF DESCRIPTION OF THE PHOTOGRAPHS

The accompanying photographs illustrate the overall appearance of the new *Lavandula* plant showing the colors as true as it is reasonably possible to obtain in colored reproductions of this type. Colors in the photographs may differ slightly from the color values cited in the detailed botanical description which accurately describe the colors of the new *Lavandula* plant.

The photograph on the first sheet is a side perspective view of a typical plant of 'Momparler' grown in a container.

The photograph on the second sheet is a close-up view of a typical inflorescence of 'Momparler'.

The photograph on the third sheet is a close-up view of typical leaves of 'Momparler'.

DETAILED BOTANICAL DESCRIPTION

The aforementioned photographs, following observations and measurements describe plants grown during the late summer in 10.5-cm containers in an outdoor nursery in Aielo de Rugat, Valencia, Spain and under environmental conditions and cultural practices which approximate those generally used in commercial *Lavandula* production. During the production of the plants, day temperatures averaged 24° C., night temperatures averaged 16° C. and light levels averaged 40 kilolux. Plants were six months old when the photographs and description were taken. In the following description, color references are made to The Royal Horticultural Society Colour Chart, 2007 Edition, except where general terms of ordinary dictionary significance are used.

Botanical classification: *Lavandula angustifolia* 'Momparler'.

Parentage: Naturally-occurring branch mutation of an unnamed selection of *Lavandula angustifolia*, not patented.

Propagation:

*Type*.—Vegetative cuttings.

*Time to initiate roots, summer*.—About 15 days at 30° C.

*Time to initiate roots, winter*.—About 23 days at 20° C.

*Time to produce a rooted young plant, summer*.—About 20 days at 30° C.

*Time to produce a rooted young plant, winter*.—About 30 days at 20° C.

*Root description*.—Fine, fibrous; bone white in color.

*Rooting habit*.—Moderately freely branching; medium density.

Plant description:

*Plant and growth habit*.—Herbaceous perennial; compact and upright plant habit; inverted triangle; moderately vigorous growth habit; rapid growth rate.

*Branching habit*.—Freely basal branching habit, dense and bushy plant form; pinching enhances secondary branching potential.

*Plant height*.—About 45 cm to 80 cm.

*Plant width* (*spread*).—About 25 cm to 40 cm.

*Lateral branch description*.—Length: Primary branches, about 45 cm to 80 cm; secondary branches, about 25 cm. Diameter: About 2.5 mm to 4.5 mm. Internode length: About 1.5 cm to 10.5 cm. Strength: Strong. Texture, young stems: Densely pubescent. Texture, mature stems: Woody, glabrous. Color, immature: Close to 138C. Color, mature: Close to 164B.

*Foliage description*.—Arrangement: Opposite, simple; sessile. Length: About 2.5 cm to 5.5 cm. Width: About 2.5 mm to 4 mm. Shape: Lanceolate to oblong. Apex: Acute. Base: Cuneate. Margin: Entire. Texture, upper and lower surfaces: Pubescent. Fragrance: Aromatic, pungent. Venation pattern: Pinnate. Color: Developing leaves, upper and lower surfaces: Close to 191C; towards the margins and apex, close to 2C. Fully expanded leaves, upper and lower surfaces: Close to 194A; venation, close to 192B.

Flower description:

*Flower arrangement and shape*.—Single sessile flowers arranged in verticillasters on spikes; freely flowering habit, about 36 to 54 flowers per inflorescence; flowers salverform with a two-lobed upper lip and a three-lobed lower lip.

*Natural flowering season*.—Plants flower continuously from May to June in Spain.

*Flower longevity on the plant*.—Flowers last about 40 days; longevity of individual flowers is highly dependent on weather conditions; flowers not persistent; terminal flower bracts persistent.

*Fragrance*.—Very fragrant.

*Inflorescence size*.—Height: About 8 cm to 12.5 cm. Diameter: About 1 cm to 3 cm.

*Flowers*.—Diameter: About 6.5 mm to 8 mm. Depth (height): About 9.5 mm to 10.5 mm.

*Petals*.—Lip length from petal base to apex: About 1.1 cm to 1.2 cm. Lip width, at the base of lobe: About 1.7 mm to 2.5 mm. Lip shape: Roughly spatulate to rounded. Lip: Rounded. Lip margin: Entire. Lip texture, upper and lower surfaces: Pubescent. Lip color: When opening, upper and lower surfaces: Close to 94B. Fully opened, upper and lower surfaces: Close to 94B; color becoming closer to 93B with development.

*Sepals*.—Arrangement: Five sepals fused into a star-shaped tube. Length: About 5.3 mm to 6.3 mm. Width: About 1.8 mm to 2.2 mm. Shape: Roughly deltoid. Apex: Rounded. Margin: Entire. Texture, upper and lower surfaces: Pubescent. Color, upper surface: Close to 142A. Color, lower surface: Close to 122A.

*Peduncles*.—Length: About 23 cm. Diameter: About 1.5 mm to 2.5 mm. Strength: Moderately strong. Aspect: Mostly erect. Color: Close to 191B.

*Pedicels*.—Length: About 1 mm to 1.5 mm. Diameter: About 0.5 mm to 0.6 mm. Strength: Moderately strong. Aspect: About 45° from the peduncle axis. Color: Close to 122D.

*Reproductive organs*.—Stamens: Quantity per flower: Four. Filament length: About 1.5 mm to 2.3 mm. Filament color: Close to 91A. Anther size: About 0.8 mm by 0.5 mm. Anther shape: Roughly reniform. Anther color: Close to 163B. Pollen amount: Moderate. Pollen color: Close to 4D. Pistils: Quantity per flower: One. Pistil length: About 5.4 mm to 5.6 mm. Stigma shape: Lanceolate. Stigma color: Close to 92A. Style length: About 4.5 mm to 4.8 mm. Style color: Close to 155C to 155D. Ovary color: Close to 142C. Fruits: Length: About 2 mm to 2.3 mm. Diameter: About 1.2 mm. Color: Close to 199A.

Disease/pest resistance: Plants of the new *Lavandula* have not been noted to be resistant to pathogens and pests common to *Lavandula*.

Garden performance: Plants of the new *Lavandula* have exhibited good tolerance to rain, wind and temperatures ranging from about −9° C. to about 40° C.

It is claimed:

1. A new and distinct *Lavandula* plant named 'Momparler' as illustrated and described.

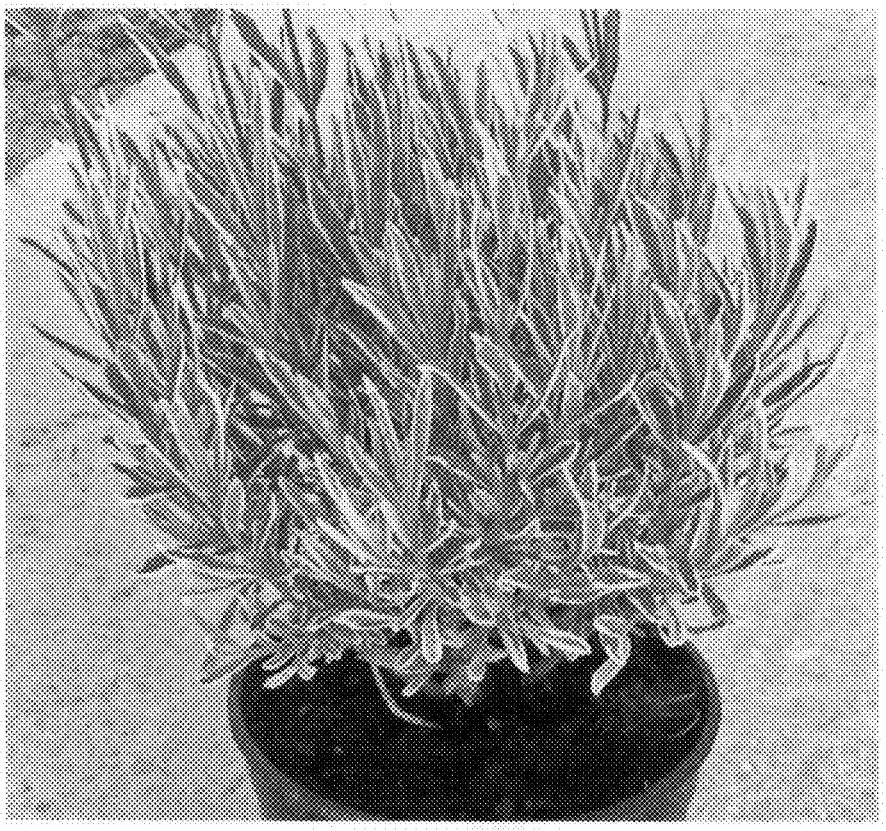

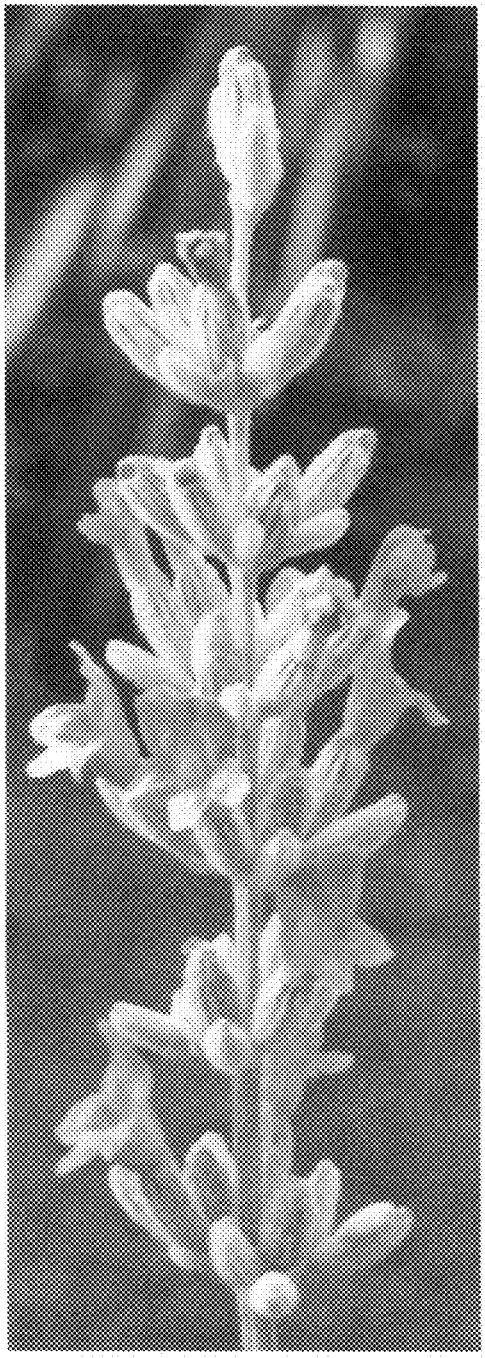

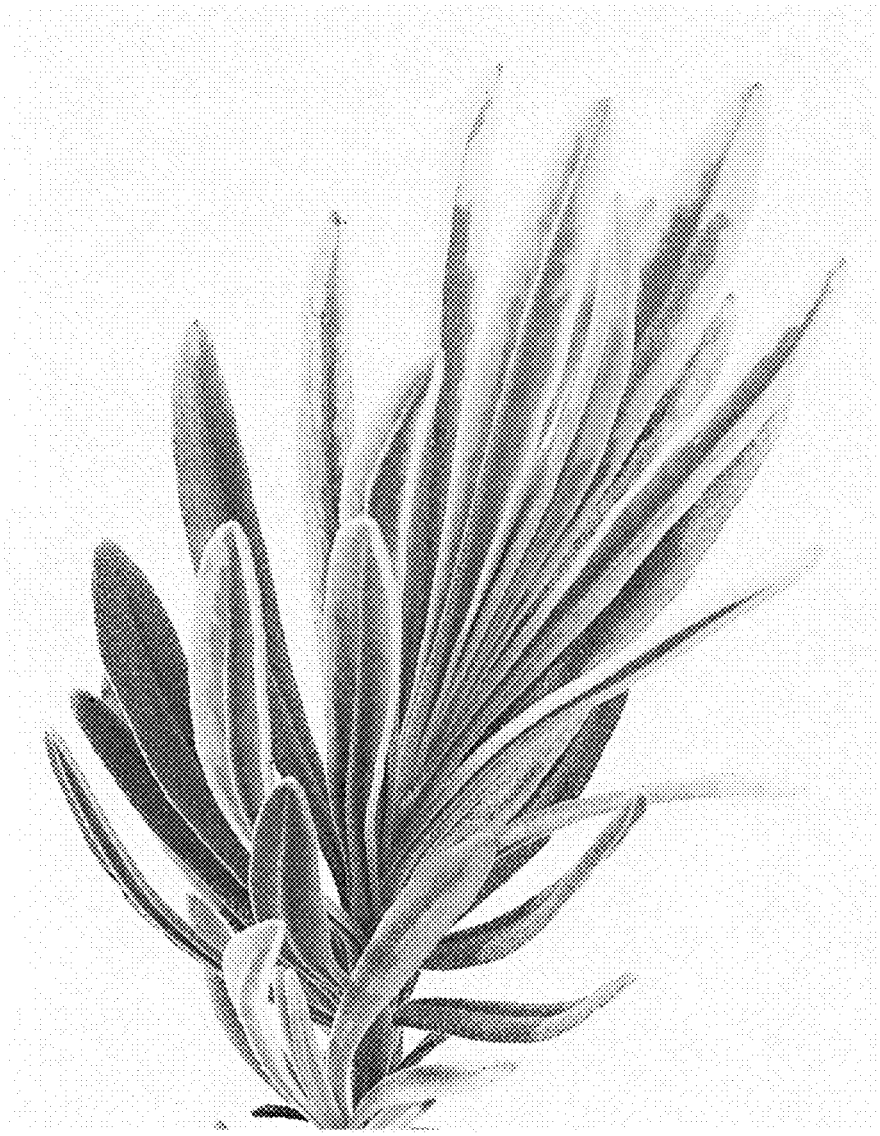

* * * * *